(12) United States Patent
Liu et al.

(10) Patent No.: US 11,826,325 B2
(45) Date of Patent: Nov. 28, 2023

(54) USE OF BELINOSTAT OR PHARMACEUTICALLY ACCEPTABLE SALT THEREOF IN PREPARATION OF DRUG FOR TREATING INFECTION

(71) Applicants: Huawei Cloud Computing Technologies Co., Ltd., Guizhou (CN); The First Affiliated Hospital of Xi'an Jiao Tong University, Xi'an (CN)

(72) Inventors: Bing Liu, Xi'an (CN); Denghui Liu, Shenzhen (CN); Xin Wang, Xi'an (CN); Peipei Zhang, Xi'an (CN); Yawen Wang, Xi'an (CN); Chi Xu, Gui'an (CN); Nan Qiao, Beijing (CN)

(73) Assignees: Huawei Cloud Computing Technologies Co., Ltd., Guizhou (CN); The First Affiliated Hospital of Xi'an Jiao Tong University, Xi'an (CN)

( * ) Notice: Subject to any disclaimer, the term of this patent is extended or adjusted under 35 U.S.C. 154(b) by 0 days.

(21) Appl. No.: 17/860,889

(22) Filed: Jul. 8, 2022

(65) Prior Publication Data
US 2022/0362183 A1    Nov. 17, 2022

Related U.S. Application Data

(63) Continuation of application No. PCT/CN2022/085168, filed on Apr. 2, 2022.

(30) Foreign Application Priority Data

Apr. 25, 2021   (CN) .......................... 202110448865.4
Mar. 29, 2022   (CN) .......................... 202210326001.X

(51) Int. Cl.
   *A61K 31/18*   (2006.01)
   *A61P 31/04*   (2006.01)

(52) U.S. Cl.
   CPC .............. *A61K 31/18* (2013.01); *A61P 31/04* (2018.01)

(58) Field of Classification Search
   None
   See application file for complete search history.

(56) References Cited

FOREIGN PATENT DOCUMENTS

| CN | 104902900 A | 9/2015 | | |
|---|---|---|---|---|
| WO | 2014061825 A1 | 4/2014 | | |
| WO | 2017009373 A1 | 1/2017 | | |
| WO | WO 2017/009373 A1 | * | 1/2017 | ............. A61K 45/06 |
| WO | WO 2019/140296 A1 | * | 7/2019 | ............. A61K 38/17 |
| WO | 2019245993 A1 | 12/2019 | | |
| WO | WO 2021/247601 A1 | * | 12/2021 | ............. A61P 11/00 |

OTHER PUBLICATIONS

Chua et al., International Journal for Parasitology: Drugs and Drug Resistance 7 (2017), pp. 42-50.*
Vanheer et al., ACS Infectious Diseases (2021), 7, pp. 2277-2284.*
Zhang et al., "1H, 130 and 15N NMR assignments of Bacillus subtilis bacteriophage SPO1 protein Gp46," Biomolecular NMR Assignments, https://doi.org/10.1007/s12104-019-09885-y, Total 3 pages (Mar. 4, 2019).
Traisaeng et al., "A Derivative of Butyric Acid, the Fermentation Metabolite of *Staphylococcus epidermidis*, Inhibits the Growth of a *Staphylococcus aureus* Strain Isolated from Atopic Dermatitis Patients," Toxins 2019, 11, 311; doi:10.3390/toxins11060311, total 12 pages (May 31, 2019).
Zhang et al. "Bacteriophage protein Gp46 is a cross-species inhibitor of nucleoid-associated HU proteins," PNAS 2022 vol. 119 No. 9 e2116278119, Total 11 pages (Jan. 14, 2022).
Chua et al., "Effect of clinically approved HDAC inhibitors on Plasmodium, Leishmania and Schistosoma parasite growth," International Journal for Parasitology: Drugs and Drug Resistance,Total 9 pages (2017).
Quah et al., "Repurposing Belinostat for Alleviation of Atopic Dermatitis," Dermatol Ther (Heidelb) (2021) 11:655 660, https://doi.org/10.1007/s13555-021-00527-7, total 6 pages (Apr. 14, 2021).
Rasmussen et al., "Comparison of HDAC inhibitors in clinical development: Effect on HIV production in latently Infected cells and T-cell activation," Human Vaccines & Immunotherapeutics, vol. 9, No. 5, XP055134827, Total 9 pages (May 1, 2013).
Kozlov et al.,"Synthesis of N'-propylhydrazide analogs of hydroxamic inhibitors of histone deacetylases (HDACs) and evaluation of their impact on activities of HDACs and replication of hepatitis C virus (HCV)," Bioorganic & Medicinal Chemistry Letters, vol. 29, No. 16, XP085758986, Total 6 pages (Jun. 5, 2019).
Agapova et al., "Inhibitor Targeting the Interface between Monomers of HU Protein from Spiroplasma melliferum Disrupts Conformational Dynamics and DNA-Binding Properties of the Protein," Crystallography Reports, vol. 65, No. 6, XP037301799, Total 6 pages (Jun. 2020).
Agapova et al., "Structure-based inhibitors targeting the alpha-helical domain of the Spiroplasma melliferum histone-like HU protein," Scientific Reports, vol. 10, No. 1, XP93079416, Total 16 pages (Sep. 15, 2020).
Bhowmick et al., "Targeting Mycobacterium tuberculosis nucleoid-associated protein HU with structure-based inhibitors," Nature Communications, vol. 5, No. 1, XP93079411, pp. 1-13 (Jun. 11, 2014).

* cited by examiner

*Primary Examiner* — Brian J Davis
(74) *Attorney, Agent, or Firm* — Leydig, Voit & Mayer, Ltd.

(57) ABSTRACT

Disclosed is the use of Belinostat or a pharmaceutically acceptable salt thereof in preparation of a drug for treating an infection. Also disclosed are related methods and compositions.

20 Claims, 8 Drawing Sheets
Specification includes a Sequence Listing.

FIG. 1

| | | | | | | | | |
|---|---|---|---|---|---|---|---|---|
| Bacillus subtilis | 70 | E | | A | | V | P | F | 79 |
| Staphylococcus aureus | 70 | D | | A | | V | P | F | 79 |
| Escherichia coli | 70 | T | | A | A | V | P | S | F | 79 |
| Klebsiella pneumoniae | 70 | T | | A | A | V | P | G | F | 79 |
| Clostridium tetani | 70 | | | E | T | V | P | V | F | 79 |
| Clostridium botulinum | 70 | T | | A | I A | P | V | F | 79 |
| Bacillus cereus | 70 | | | A | | V | P | F | 79 |
| Bacillus anthracis | 70 | | | | | V | P | F | 79 |
| Acinetobacter baumannii | 70 | | K | A | T | V | P | S | F | 79 |

FIG. 2

DNA-binding protein HU  Bacillus subtilis (Bacillus subtilis)
GenBank: CUB54458.1

DNA-binding protein HU  Staphylococcus aureus (Staphylococcus aureus)
GenBank: BCN35037.1

DNA-binding protein HU  Escherichia coli (Escherichia coli)
GenBank: ALQ73741.1

DNA-binding protein HU  Klebsiella pneumoniae (Klebsiella pneumoniae)
GenBank: AUC28750.1

DNA-binding protein HU  Clostridium tetani (Clostridium tetani)
GenBank: SUY58139.1

DNA-binding protein HU  Clostridium botulinum (Clostridium botulinum)
GenBank: APC82021.1

DNA-binding protein HU  Bacillus cereus (Bacillus cereus)
GenBank: ETT81897.1

DNA-binding protein HU  Bacillus anthracis (Bacillus anthracis)
GenBank: BBK96599.1

DNA-binding protein HU  Acinetobacter baumannii (Acinetobacter baumannii)
GenBank: ANA37532.1

FIG. 3

USE OF BELINOSTAT OR PHARMACEUTICALLY ACCEPTABLE SALT THEREOF IN PREPARATION OF DRUG FOR TREATING INFECTION

CROSS-REFERENCE TO RELATED APPLICATIONS

This application is a continuation of International Patent Application PCT/CN2022/085168, filed on Apr. 2, 2022, which claims priority to Chinese Patent Application No. 202210326001.X, filed on Mar. 29, 2022 and Chinese Patent Application No. 202110448865.4, filed on Apr. 25, 2021. All of the aforementioned patent applications are hereby incorporated by reference in their entireties.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 25,874 Byte XML file named "763462_ST26.xml," dated Jul. 28, 2022.

TECHNICAL FIELD

The present invention relates to the field of medicines, and in particular, to use of Belinostat or a pharmaceutically acceptable salt thereof in preparation of a drug for treating an infection.

BACKGROUND

Belinostat was approved by the FDA on Jul. 3, 2014 for treatment of peripheral T-cell lymphoma (PTCL). At present, Belinostat is further being examined for the treatment of other tumors. Belinostat(N-hydroxy-3-(3-[(phenylamino)sulfonyl]phenyl)acrylamide) has the following chemical structural formula:

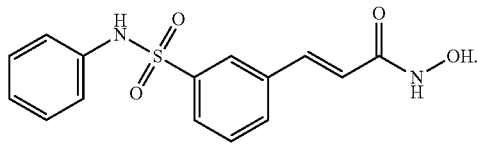 [SMILES: O=C(/C=C/c1cccc(S(=O)(=O)Nc2ccccc2)c1)NO]

Infections, such as bacterial infections, seriously endanger human health. Although antibiotics can effectively treat many bacterial infections, drug-resistant or even multi-drug-resistant bacteria emerge continuously, making originally effective antibiotics ineffective. For example, *Bacillus subtilis* is resistant to sulfamethazine and oxytetracycline; and *Staphylococcus aureus* is resistant to many penicillins and cephalosporins. Bacterial infections with drug resistance or even multi-drug resistance have become a major threat to human health.

Clinically, there is significant demand for drugs that can treat infections, especially drugs that kill drug-resistant/multi-drug-resistant bacteria.

SUMMARY

It is known in the art that bacteriophages, as bacterial viruses, can specifically infect and lyse host bacteria. Surprisingly and unexpectedly, the inventor of the present application found that bacteriophages expressing a Gp46 protein can occupy a DNA binding region of a bacterial HU protein, thereby blocking participation of the HU protein in bacterial DNA replication by inhibiting binding of the HU protein to a bacterial DNA, finally leading to bacterial death. By studying a Gp46-HU protein binding site, the present inventor found that isoleucine (Ile) at a $71^{st}$ site of the bacterial HU protein not only is involved in a reaction between the HU protein and the Gp46 protein, but also is a key site for binding of the HU protein to the DNA. Surprisingly and unexpectedly, the present inventor also found that Belinostat can bind to a drug-resistant bacterial HU protein, especially can bind to isoleucine (Ile) at the $71^{st}$ site of the HU protein, and then kill bacteria (including superbacteria).

With the help of computer software, the present inventor performed molecular dynamics simulation calculation on a drug candidate region in the DrugBank drug database, and screened candidate drugs. Surprisingly and unexpectedly, the present inventor found that Belinostat and a pharmaceutically acceptable salt thereof can achieve high binding activity with isoleucine at the $71^{st}$ site of the bacterial HU protein, thereby blocking participation of the HU protein in bacterial DNA replication by inhibiting binding of the HU protein to the bacterial DNA, finally leading to bacterial death.

The present inventor found that the HU protein is a highly conserved protein in bacteria. In other normal bacteria and clinically common drug-resistant bacteria with a very high mutation rate, such as key clinically pathogenic bacteria like *Mycobacterium tuberculosis, Staphylococcus aureus*, and *Acinetobacter baumannii*, this key amino acid site has also been completely retained. Therefore, drugs targeting this site have broad-spectrum antibacterial properties and are effective against drug-resistant bacteria. Belinostat can also bind to a HU protein (such as isoleucine (Ile) at the $71^{st}$ site) of drug-resistant bacteria/multi-drug-resistant bacteria with high binding activity. As such, Belinostat has a strong inhibitory effect on superbacteria and exhibits a good bactericidal effect.

The present inventor found that a minimum inhibitory concentration (MIC) of Belinostat or a pharmaceutically acceptable salt thereof is less than or equal to about 100 μM, less than or equal to about 50 μM, or less than or equal to about 10 μM (for example, 9 μM, 8 μM, 7 μM, 6 μM, 5 μM, 4 μM, 3 μM, 2 μM, or 1 μM), preferably less than or equal to about 1 μM (for example, less than or equal to 0.9 μM, 0.8 μM, 0.7 μM, 0.6 μM, 0.5 μM, 0.4 μM, 0.3 μM, 0.2 μM, or 0.1 μM), more preferably less than or equal to 0.1 μM (for example, less than or equal to 0.09 μM, 0.08 μM, 0.07 μM, 0.06 μM, 0.05 μM, 0.04 μM, 0.03 μM, 0.02 μM, or 0.01 μM).

The present application provides use of Belinostat or a pharmaceutically acceptable salt thereof in preparation of a drug for treating an infection. In an exemplary embodiment of the present application, Belinostat or the pharmaceutically acceptable salt thereof can be used to treat an infection (for example, a bacterial (including superbacteria) infection). In an exemplary embodiment of the present application, Belinostat or the pharmaceutically acceptable salt thereof has a significant inhibitory effect on bacteria (including superbacteria).

In another exemplary embodiment of the present application, a pharmaceutical composition is provided, which includes Belinostat or a pharmaceutically acceptable salt thereof and optionally includes a pharmaceutically acceptable carrier.

BRIEF DESCRIPTION OF DRAWINGS

FIG. 1 illustrates a sequence alignment result of complete sequences of a plurality of bacterial HU proteins (SEQ ID NOS: 1-9);

FIG. 2 illustrates a sequence alignment result of a plurality of bacterial HU proteins (SEQ ID NOS: 10-18) near isoleucine at a $71^{st}$ site;

FIG. 3 illustrates GenBank numbers of HU proteins (SEQ ID NOS: 19-27) in related bacteria in FIG. 1 and FIG. 2;

FIG. 10A to FIG. 10D show a blank control group, a high-concentration Belinostat group, a low-concentration Belinostat group, and a fusidic acid group, respectively.

Figure 4:
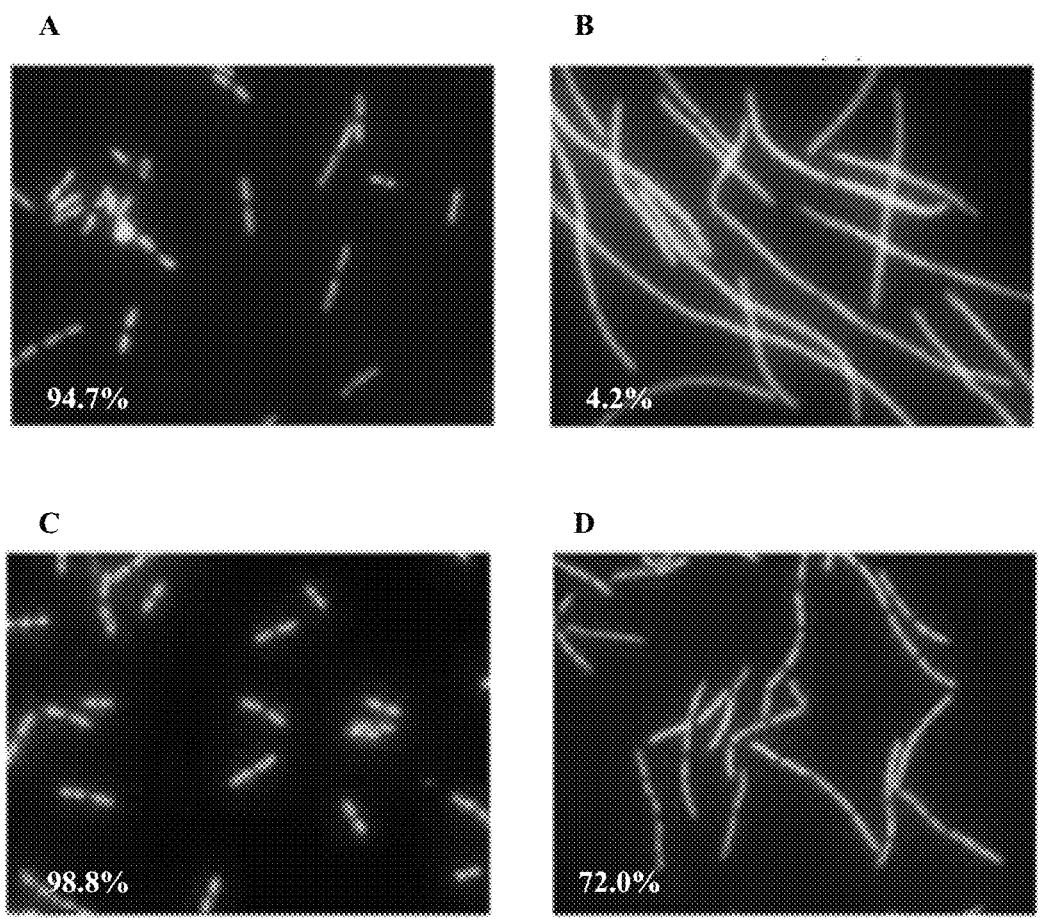
FIG. 4 illustrates a morphology of *Bacillus subtilis* and a percentage of cells with normal nucleoids in total cells in a visual field under different conditions.

In an aspect, the present invention provides use of Belinostat or a pharmaceutically acceptable salt thereof in preparation of a drug for treating an infection, wherein the drug optionally includes a pharmaceutically acceptable carrier. In another aspect, the present invention provides Belinostat or a pharmaceutically acceptable salt thereof for treating an infection. In another aspect, the present invention provides a method for treating an infection, including administering a therapeutically effective amount of Belinostat or a pharmaceutically acceptable salt thereof to a subject in need.

In an exemplary embodiment of the present application, the infection includes, but is not limited to: a skin infection, a gastrointestinal infection, a urinary tract infection, a genitourinary tract infection, a respiratory tract infection, a sinus infection, a middle ear infection, a systemic infection, a wound infection, a central nervous system infection, an intra-abdominal infection, pyelonephritis, pneumonia, bacterial vaginosis, streptococcal sore throat, chronic bacterial prostatitis, a gynecological and pelvic infection, a sexually transmitted bacterial disease, and eye and ear infections. In an exemplary embodiment of the present application, the infection may be a bacterial infection, a fungal infection, a parasitic infection, or a viral infection.

In an embodiment, the infection is a respiratory tract infection. In a specific aspect, the respiratory tract infection is community-acquired bacterial pneumonia (CABP). In an embodiment, the respiratory tract infection such as the CABP is caused by bacteria selected from the following: *Staphylococcus aureus* (*S. aureus*), *Streptococcus pneumoniae* (*S. pneumoniae*), *Streptococcus pyogenes* (*S. pyogenes*), *Haemophilus influenzae* (*H. influenzae*), *Moraxella catarrhalis* (*M. catarrhalis*), and *Legionella pneumophila* (*Legionella pneumophila*).

In an embodiment, the infection is a skin infection. In a specific aspect, the skin infection is an acute bacterial skin and skin structure infection (ABSSSI). In an embodiment, the skin infection such as the ABSSSI is caused by bacteria selected from the following: *Staphylococcus aureus*, CoNS, *Streptococcus pyogenes*, *Streptococcus agalactiae* (*S. agalactiae*), *Enterococcus faecalis* (*E. faecalis*), and *Enterococcus faecium* (*E. faecium*).

In an embodiment, the infection may be caused by bacteria (such as anaerobic bacteria or aerobic bacteria).

In an embodiment, the infection is caused by gram-positive bacteria. In an aspect of this embodiment, the infection is caused by gram-positive bacteria selected from the following: Bacilli (Bacilli), including but not limited to *Staphylococcus* spp. (*Staphylococcus* spp.), *Enterococcus* spp. (*Enterococcus* spp.), *Bacillus* spp. (*Bacillus* spp.), and *Listeria* spp. (*Listeria* spp.); phylum Actinobacteria (phylum Actinobacteria), including but not limited to *Propionibacterium* spp. (*Propionibacterium* spp.), *Corynebacterium* spp. (*Corynebacterium* spp.), *Nocardia* spp. (*Nocardia* spp.), and Actinobacteria spp. (Actinobacteria spp.); and Clostridia, including but not limited to *Clostridium* spp. (*Clostridium* spp.).

In an embodiment, the infection is caused by gram-positive bacteria selected from the following: *Staphylococcus aureus*, *Streptococcus pneumoniae*, *Streptococcus pyogenes*, *Streptococcus agalactiae*, *Enterococcus faecalis*, and *Enterococcus faecium*.

In an embodiment, the infection is caused by gram-negative bacteria. In an aspect of this embodiment, the infection is caused by the following bacteria: proteobacteria (proteobacteria) (such as Betaproteobacteria (Betaproteobacteria) and Gammaproteobacteria (Gammaproteobacteria)), including *Escherichia coli* (*Escherichia coli*), *Salmonella* (*Salmonella*), *Shigella* (*Shigella*), other Enterobacteriaceae (Enterobacteriaceae), *Pseudomonas* (*Pseudomonas*), *Moraxella* (*Moraxella*), *Helicobacter* (*Helicobacter*), *Stenotrophomonas* (*Stenotrophomonas*), Bdellovibrio (Bdellovibrio), acetic acid bacteria (acetic acid bacteria), and *Legionella* (*Legionella*); or Alphaproteobacteria, such as *Wolbachia* (*Wolbachia*). In another aspect, the infection is caused by gram-negative bacteria selected from cyanobacteria, spirilla, green sulfur bacteria, or green non-sulfur bacteria. In an aspect of this embodiment, the infection is caused by gram-negative bacteria selected from the following: Enterobactericeae (Enterobactericeae) (for example, *Escherichia coli* (*E. coli*), *Klebsiella pneumoniae* (*Klebsiella pneumoniae*), including *Escherichia coli* and *Klebsiella pneumoniae* containing extended spectrum beta-lactamases and/or carbapenemases), Bacteroidaceae (Bacteroidaceae) (such as *Bacteroides fragilis* (*Bacteroides fragilis*)), Vibrionaceae (Vibrionaceae) (*Vibrio cholerae* (*Vibrio cholerae*)), Pasteurellae (Pasteurellae) (such as *Haemophi-* lus influenzae (*Haemophilus influenzae*)), Pseudomonadaceae (Pseudomonadaceae) (such as *Pseudomonas aeruginosa* (*Pseudomonas aeruginosa*)), Neisseriaceae (Neisseriaceae) (such as *Neisseria meningitidis* (*Neisseria meningitidis*)), Rickettsiae (Rickettsiae), Moraxellaceae (Moraxellaceae) (such as *Moraxella catarrhalis* (*Moraxella catarrhalis*)), any species of Proteeae (Proteeae), *Acinetobacter* spp. (*Acinetobacter* spp.), *Helicobacter* spp. (*Helicobacter* spp.), and *Campylobacter* spp. (*Campylobacter* spp.). In an embodiment, the infection is caused by gram-negative bacteria selected from Enterobactericeae (such as *Escherichia coli* and *Klebsiella pneumoniae*), *Pseudomonas*, and *Acinetobacter* spp. In an embodiment, the infection is caused by an organism selected from the following: *Klebsiella pneumoniae* (*K. pneumoniae*), *Salmonella* (*Salmonella*), *E. hirae* (*E. hirae*), *Acinetobacter baumannii* (*A. baumannii*), *Moraxella catarrhalis* (*M. catarrhalis*), *Haemophilus influenzae* (*H. influenzae*), *Pseudomonas aeruginosa* (*P. aeruginosa*), *Enterococcus faecium*, *Escherichia coli*, *Staphylococcus aureus*, and *Enterococcus faecalis*.

In an embodiment, the infection is caused by gram-negative bacteria selected from *Haemophilus influenzae, Moraxella catarrhalis*, and *Legionella pneumophila*.

In an embodiment, the infection is caused by one or more selected from the group consisting of *Bacillus subtilis, Mycobacterium tuberculosis, Staphylococcus aureus*, and *Acinetobacter baumannii*.

In an embodiment, the infection is caused by *Bacillus anthracis* (*Bacillus anthracis*) (anthrax), *Yersinia pestis* (*Yersinia pestis*) (plague), *Clostridium botulinum* (*Clostridium botulinum*) (botulism), or *Francisella tularensis* (*Francisella tularensis*) (tularemia). In exemplary embodiments of the present application, Belinostat or the pharmaceutically acceptable salt thereof can be used to treat additional infections, such as but not limited to, anthrax, botulism, bubonic plague, and tularemia.

In an embodiment, the infection is caused by an organism (such as a bacterium) that is resistant to one or more antibiotics.

In an embodiment, the infection is caused by an organism that is resistant to tetracycline or any member of first and second generation tetracycline antibiotics (such as doxycycline or minocycline).

In an embodiment, the infection is caused by an organism that is resistant to methicillin.

In an embodiment, the infection is caused by an organism that is resistant to vancomycin.

In an embodiment, the infection is caused by an organism that is resistant to a quinolone or a fluoroquinolone.

In an embodiment, the infection is caused by an organism that is resistant to tigecycline (tigecycline) or any other tetracycline derivative. In an embodiment, the infection is caused by an organism that is resistant to tigecycline.

In an embodiment, the infection is caused by an organism resistant to beta-lactams or cephalosporins or an organism resistant to penems or carbapenems.

In an embodiment, the infection is caused by an organism resistant to macrolide, lincosamides (lincosamides), streptogramins, oxazolidone, and pleuromutilin.

In an embodiment, the infection is caused by a multi-drug-resistant pathogen (moderately or completely resistant to any two or more antibiotics).

In an exemplary embodiment of the present application, the organism may be bacteria, fungi, viruses, or the like.

In an exemplary embodiment of the present application, examples of the infection in the present application include, but are not limited to, intra-abdominal infections (usually a mixture of gram-negative bacteria such as *Escherichia coli* and anaerobic bacteria such as *Bacteroides fragilis*), diabetic foot (various combinations of *Streptococcus, Serratia, Staphylococcus* and *Enterococcus*, and anaerobic bacteria (S. E. Dowd et al., PloS one 2008; 3: e3326, the entire teachings of which are incorporated herein by reference), respiratory diseases (especially respiratory system diseases in patients with chronic infections such as cystic fibrosis, for example, *Staphylococcus aureus* plus *Pseudomonas aeruginosa* or *Haemophilus influenzae*, and atypical pathogens), wounds and abscesses (various gram-negative and gram-positive bacteria, especially MSSA/MRSA, coagulase-negative *Staphylococcus*, enterococcus, *Acinetobacter, Pseudomonas aeruginosa* (*P. aeruginosa*), *Escherichia coli*, and *Bacteroides fragilis*), and bloodstream infections (13% are multi-microbial infections (H. Wisplinghoff et al., Clin. Infect. Dis. 2004; 39: 311-317, the entire teachings of which are incorporated herein by reference)).

Belinostat can react with various acids or bases to form salts. Generally, acids used to form acidic salts are inorganic acids such as hydrochloric acid, hydrobromic acid, hydroiodic acid, sulfuric acid, and phosphoric acid, or organic acids such as p-toluenesulfonic acid, methanesulfonic acid, oxalic acid, p-bromobenzenesulfonic acid, carbonic acid, succinic acid, citric acid, benzoic acid, and acetic acid. Examples of these salts include a sulfate, a pyrosulfate, a bisulfate, a sulfite, a bisulfate, a phosphate, a monohydrogen phosphate, a dihydrogen phosphate, a metaphosphate, a pyrophosphate, a chloride, a bromide, an iodide, an acetate, a propionate, a caprate, a caprylate, an acrylate, a formate, an isobutyrate, a caproate, a heptanoate, a propiolate, an oxalate, a malonate, a succinate, a suberate, a sebacate, a fumarate, a maleate, butene-1,4-diacid, hexene-1,6-diacid, benzoate, chlorobenzoate, methylbenzoate, dinitrobenzoate, hydroxybenzoate, methoxybenzoate, phthalate, tartrate, methanesulfonate, propanesulfonate, naphthalene-1-sulfonate, naphthalene-2-sulfonate, mandelate, and the like. Alkaline salts may be generated from inorganic bases, such as a hydroxides, carbonates, and bicarbonates of ammonium, alkali metals or alkaline earth metals. The following alkaline substances, for example, sodium hydroxide, potassium hydroxide, calcium hydroxide, ammonium hydroxide, and potassium carbonate, are often used to form alkaline salts. Examples of these salts include sodium salt, potassium salt, calcium salt, magnesium salt, ammonium salt, and the like.

Exemplary embodiments of the present application further provide a pharmaceutical composition which includes Belinostat or a pharmaceutically acceptable salt thereof and optionally a pharmaceutically acceptable carrier. In the present invention, the pharmaceutical composition may be a tablet, a capsule, a granule, a syrup, a suspension, a solution, a dispersant, a sustained-release preparation for oral or non-oral administration, an intravenous preparation, a subcutaneous preparation, an inhalant, a transdermal preparation, or a rectal or vaginal suppository.

In exemplary embodiments of the present application, the pharmaceutically acceptable carrier refers to a pharmaceutically acceptable carrier known by a person skilled in the art. The pharmaceutically acceptable carrier in the present application includes, but is not limited to, a filler, a wetting agent, an adhesive, a disintegrant, a lubricant, a binder, a glidant, a taste masking agent, a surfactant, and a preservative. The filler includes, but is not limited to, lactose, microcrystalline cellulose, starch, powdered sugar, dextrin, mannitol, and calcium sulfate. The wetting agent and the adhesive include, but are not limited to, sodium carboxymethyl cellulose, hydroxypropyl cellulose, hydroxypropyl methylcellulose, gelatin, sucrose, and polyvinylpyrrolidone. The disintegrant includes, but is not limited to, sodium carboxymethyl starch, cross-linked polyvinylpyrrolidone, cross-linked sodium carboxymethyl cellulose, and low-substituted hydroxypropyl cellulose. The lubricant includes, but is not limited to, magnesium stearate, micronized silica gel, talc, hydrogenated vegetable oil, polyethylene glycol, and magnesium lauryl sulfate. The binder includes, but is not limited to, gum Arabic, alginic acid, calcium carboxymethylcellulose, sodium carboxymethylcellulose, dextrates, dextrin, dextrose, ethyl cellulose, gelatin, liquid glucose, guar gum, hydroxyethyl cellulose, hydroxypropyl cellulose, hydroxypropyl methylcellulose, magnesium aluminum silicate, maltodextrin, methylcellulose, polymethacrylate, polyvinylpyrrolidone, pregelatinized starch, sodium alginate, sorbitol, starch, syrup, and gum tragacanth. The glidant includes, but is not limited to, colloidal silica, powdered cellulose, magnesium trisilicate, silica, and talc. The taste masking agent includes, but is not limited to, aspartame, stevioside, fructose, glucose, syrup, honey, xylitol, mannitol, lactose, sorbitol, maltitol, and glycyrrhizin. The surfactant includes, but is not limited to, Tween-80 and poloxamer. The preservative includes, but is not limited to, parabens, sodium benzoate, and potassium sorbate.

Methods for preparing various pharmaceutical compositions containing active ingredients in various proportions are known, or are apparent to a person skilled in the art based on the disclosure of the present application, as described in REMINGTON'S PHARMACEUTICAL SCIENCES, Martin, E. W., ed., Mack Publishing Company, 19th ed. (1995). The method for preparing the pharmaceutical composition includes mixing an appropriate pharmaceutical excipient, carrier, diluent, or the like. The pharmaceutical composition of the present invention is manufactured by using known methods, including conventional mixing, dissolving, or lyophilization methods.

In the pharmaceutical composition of the present invention, a proportion of active ingredients may vary, and the active ingredients may account for about 0.01% to about 99% of the weight of a given unit dosage form. In this therapeutically useful pharmaceutical composition preparation, an amount of the active ingredients is in such a way that an effective dosage level can be obtained.

The tablet, the capsule, and the like in the present invention may include: a binder, such as gum tragacanth, gum Arabic, corn starch, or gelatin; an excipient, such as dicalcium phosphate; a disintegrant, such as corn starch, potato starch, or alginic acid; a lubricant, such as magnesium stearate; and a sweetener, such as sucrose, fructose, lactose, or aspartame; or a flavoring agent, such as peppermint, wintergreen oil, or cherry flavor. When the unit dosage form is a capsule, the capsule may include a liquid carrier, such as vegetable oil or polyethylene glycol, in addition to the foregoing types of materials. Various other materials may be present, as coatings, or otherwise change a physical form of a solid unit dosage form. For example, the tablet or the capsule may be coated with gelatin, wax, shellac, or sugar. The syrup may include active ingredients, sucrose or fructose as a sweetener, and methyl p-hydroxybenzoate or propyl p-hydroxybenzoate as a preservative, dye, and flavoring agent (such as cherry flavor or orange flavor). As known in the art, any material used to prepare any unit dosage form should be pharmaceutically acceptable and nontoxic in an applied amount. In addition, the active ingredients may be mixed into a sustained-release preparation and a sustained-release apparatus.

The active ingredients may also be administered intravenously or intraperitoneally by infusion or injection. An aqueous solution of the active ingredients or a salt thereof may be prepared and optionally mixed with a nontoxic surfactant. A dispersant in glycerin, liquid polyethylene glycol, glycerol triacetate, and a mixture thereof, and oil may also be prepared. Under ordinary storage and use conditions, these preparations contain a preservative to prevent microbial growth.

Pharmaceutical composition dosage forms suitable for injection or infusion may include a sterile aqueous solution or dispersant or sterile powder containing active ingredients (optionally encapsulated in liposomes) suitable for an instant preparation of a sterile and injectable or infusion-ready solution or dispersant. In all cases, the final dosage form needs to be sterile, liquid, and stable under conditions of manufacture and storage. The liquid carrier may be a solvent or a liquid dispersion medium, including, for example, water, ethanol, polyhydric alcohol (for example, glycerin, propylene glycol, and liquid polyethylene glycol), vegetable oil, nontoxic glycerides, and a suitable mixture thereof. Appropriate fluidity may be maintained, for example, by formation of liposomes, by maintaining a required particle size in the presence of a dispersant, or by use of a surfactant. Microorganisms can be prevented by using various antibacterial agents and antifungal agents (such as paraben, chlorobutanol, phenol, sorbic acid, and thimerosal). In many cases, an isotonic agent, such as sugar, a buffer or sodium chloride, is preferably included. Prolonged absorption of an injectable composition can be implemented by using a composition (for example, aluminum monostearate and gelatin) that delays an absorbent.

A sterile injectable solution is prepared by combining a required amount of active ingredients in a suitable solvent with the required various other ingredients listed above, and then filtering and sterilizing. In the case of sterile powder used to prepare a sterile injection solution, preferred preparation methods are vacuum drying and freeze drying techniques, which produce powder of active ingredients plus any other required ingredients present in a sterile filtered solution.

A useful solid carrier includes a pulverized solid, such as, e.g., talc, clay, microcrystalline cellulose, silica, or alumina. A useful liquid carrier includes water, ethanol or ethylene glycol or a water-ethanol/ethylene glycol mixture, in which the pharmaceutical composition in the present invention can be dissolved or dispersed with effective content optionally with the help of a nontoxic surfactant. An adjuvant (such as fragrance) and an additional antimicrobial agent may be added to optimize properties for given use.

A thickener (such as a synthetic polymer, a fatty acid, a fatty acid salt and ester, a fatty alcohol, modified cellulose, or a modified inorganic material) may also be used with a liquid carrier to form a coatable paste, a gel, an ointment, soap, or the like, which is directly applied to skin of a user.

The therapeutically effective amount of active ingredients depends not only on a selected specific salt, but also on a mode of administration, a nature of a disease to be treated, and an age and a state of a patient, and ultimately on a decision of an attending physician or clinician.

The foregoing preparation may exist in a unit dosage form, and the unit dosage form is a physically dispersed unit containing a unit dose, and is suitable for administration to a human body and another mammal. The unit dosage form may be a capsule or a tablet. Depending on specific treatment involved, the amount of the unit dose of the active ingredients may be varied or adjusted from about 0.01 milligrams to about 1000 milligrams or more.

The term "treatment" used in the present application generally refers to obtaining a desired pharmacological and/or physiological effect. The effect may be prophylactic in terms of complete or partial prevention of a disease or a symptom thereof; and/or therapeutic in terms of partial or complete stabilization or cure of a disease and/or side effects of the disease. As used herein, "treatment" covers any treatment of a disease of a patient, including: (a) preventing a disease or a symptom of a patient who is susceptible to the disease or the symptom but has not yet been diagnosed; (b) suppressing the symptom of the disease, e.g., preventing development of the disease; or (c) alleviating the symptom of the disease, e.g., causing the disease or the symptom to degrade.

In an implementation, the organism in the present invention is a drug-resistant bacterium, such as methicillin-resistant Staphylococcus aureus (Methicillin-resistant Staphylococcus aureus, MRSA).

In an implementation, the infection in the present invention is caused by one or more bacteria selected from the group consisting of Bacillus subtilis, Mycobacterium tuberculosis, Staphylococcus aureus, and Acinetobacter baumannii.

In an embodiment, the infection in the present invention is a respiratory tract infection, a wound infection, a urinary tract infection, or a central nervous system infection.

In an embodiment, the present invention provides use of Belinostat or a pharmaceutically acceptable salt thereof in preparation of a HU protein inhibitor. Preferably, Belinostat and the pharmaceutically acceptable salt thereof can bind to isoleucine at a 71st site of an organism HU protein.

In an embodiment, the present invention provides use of a Gp46 protein (such as a bacteriophage Gp46 protein) in preparation of a HU protein inhibitor. Specifically, the inventor found that the Gp46 protein can occupy a DNA binding region of a bacterial HU protein, thereby blocking participation of the HU protein in bacterial DNA replication by inhibiting binding of the HU protein to a bacterial DNA, finally leading to bacterial death. By studying a Gp46-HU protein binding site, the inventor determined that isoleucine (Ile) at a 71st site of the bacterial HU protein not only is involved in a reaction between the HU protein and the Gp46 protein, but also is a key site for binding of the HU protein to the DNA. Surprisingly and unexpectedly, the inventor also found that Belinostat can bind to a drug-resistant bacterial HU protein, especially can bind to isoleucine (Ile) at the 71st site of the HU protein, and then kill bacteria (including superbacteria). The inventor found that, in other normal bacteria and clinically common drug-resistant bacteria with a very high mutation rate, such as key clinically pathogenic bacteria like Mycobacterium tuberculosis, Staphylococcus aureus, and Acinetobacter baumannii, this key amino acid site has also been completely retained. Therefore, drugs targeting this site have broad-spectrum antibacterial properties and are effective against drug-resistant bacteria.

In an embodiment, the bacteria in the present invention have multiple drug resistance.

The term "about", when used in conjunction with a numerical value, is meant to cover numerical values within a range having a lower limit of 5% less than the specified numerical value and an upper limit of 5% greater than the specified numerical value.

The term "comprising" or "including" means including the stated elements, integers, or steps, but not excluding any other elements, integers, or steps. Herein, when the term "comprising" or "including" is used, unless otherwise indicated, a case consisting of the mentioned elements, integers, or steps is also covered.

The term "subject" includes a mammal, and the mammal includes, but is not limited to, a domestic animal (for example, a cattle, a sheep, a cat, a dog, or a horse), a primate (for example, a human or a non-human primate such as a monkey), a rabbit, or a rodent (for example, a mouse or a rat). In embodiments, an individual or the subject is a human.

DESCRIPTION OF EMBODIMENTS

Various example embodiments, features, and aspects of the present invention are described in detail below with reference to the accompanying drawings. The word "example" used here means "serving as an example, an embodiment, or an illustration". Any embodiment described here as an "example" need not be interpreted as being superior to or better than other embodiments.

In addition, to better illustrate the present application, numerous specific details are given in the following detailed embodiments. It should be understood by a person skilled in the art that the present invention can still be implemented without some specific details. Unless otherwise defined, all technical and scientific terms used herein have the same meanings as those commonly understood by a person of ordinary skill in the art.

Experimental methods described in the following embodiments are conventional methods unless otherwise stated. Unless otherwise stated, software, reagents, and materials are commercially available. The "X" in the embodiments represents Belinostat.

Figure 1:
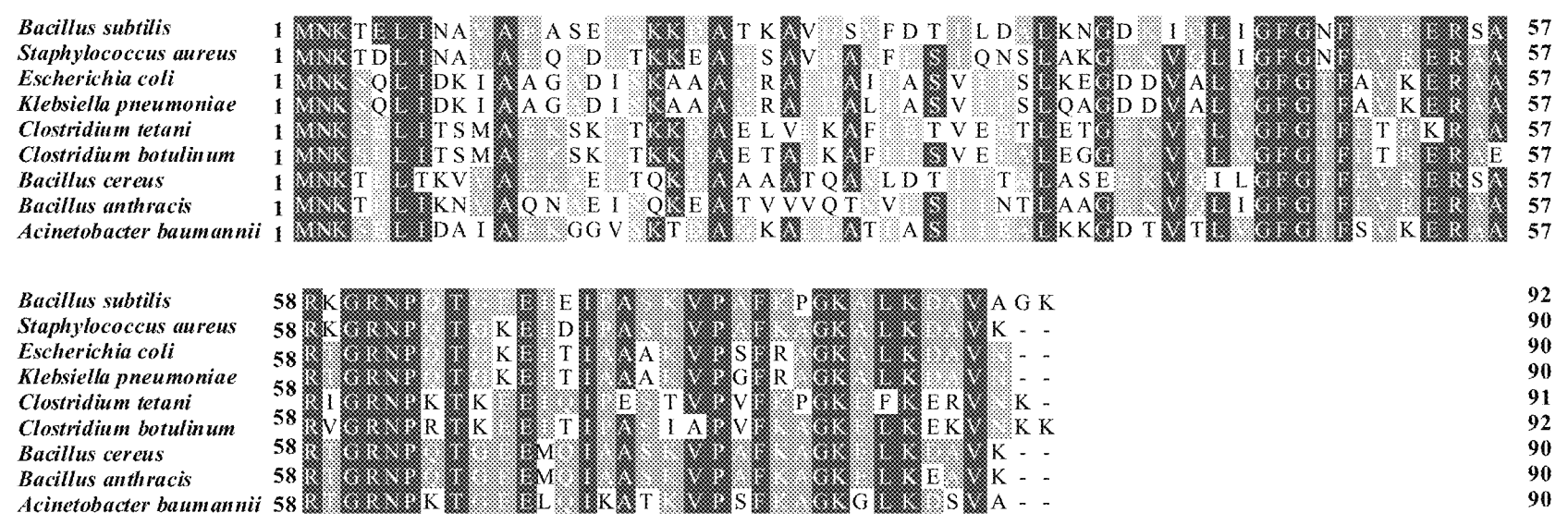

Embodiment 1: Computer-Aided Screening for Determining of Candidate Drug Belinostat (1) Determining a Target Region of Candidate Drugs Through studying of binding sites of a bacteriophage Gp46 protein and a HU protein, it was determined that isoleucine at a 71st site in the HU protein was one of the binding sites of the HU protein and the Gp46 protein. Then, the inventor compared complete sequences of HU proteins of various bacteria (FIG. 1) and found that isoleucine at a $71^{St}$ site in HU proteins of various bacteria was highly conserved (FIG. 2). A GenBank sequence number of the bacteria is shown in FIG. 3.

FIG. 4A and FIG. 4C show a morphology of normal Bacillus subtilis without HU protein mutation, and cells with normal nucleoids in a visual field accounted for 94.7% and 98.8% of total cells, respectively. FIG. 4B shows a morphology of Bacillus subtilis when a HU protein was inhibited. FIG. 4D shows a morphology of Bacillus subtilis after isoleucine at a 71st site in a HU protein was mutated to alanine. It may be learned that compared with normal Bacillus subtilis, bacteria after mutation of an amino acid at a 71st site in the HU protein became longer, a nucleoid morphology of some bacteria was destroyed (FIG. 4D), and cells with normal nucleoids in a visual field accounted for 72.0% of total cells. After the HU protein was directly inhibited, bacteria became longer obviously, and bacteria with a normal nuclear morphology were greatly reduced, accounting for only 4.2% of the total cells (FIG. 4B). This shows that the HU protein is very important for normal growth of bacteria, and the isoleucine at the 71st site of the HU protein is an important site for the HU protein to function. Therefore, the HU protein was determined as a target of candidate drugs.

Figure 5:
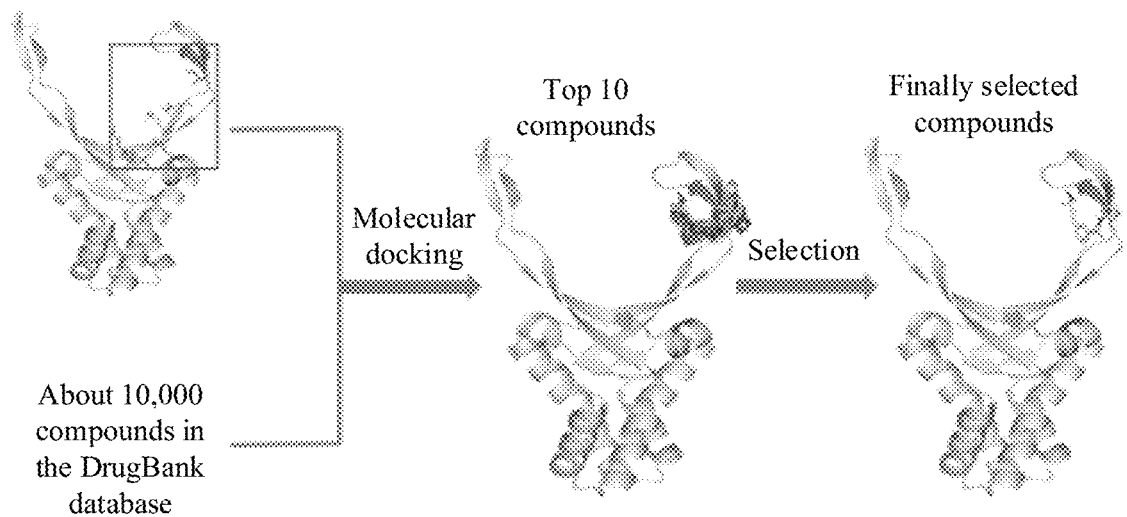
FIG. 5 is a diagram showing a principle of computer-aided screening and determining of candidate drugs.

(2) Large-Scale Drug Screening by Using Computer Software Vina for Determining of Candidate Drugs Candidate drugs were obtained from the DrugBank drug database, and molecular dynamics simulation calculation was performed on a target of the foregoing candidate drugs by using computer software Vina (FIG. 5). Results of simulation were sequenced by using Energy Value, and top 10 drugs were used as candidate drugs. Belinostat ranked $7^{th}$, with a binding energy of −4.9 (kJ/mol) and a relatively strong binding ability.

Embodiment 2: A Molecular Level Experiment Proved Binding of Belinostat and an Amino Acid at a 71st Site in a HU Protein At the molecular level, a binding effect of Belinostat with the HU protein was verified by nuclear magnetism Titration and waterLOGSY experiments. The isoleucine (Ile) at the $71^{St}$ site in the HU protein was mutated into alanine (Ala) to obtain a corresponding mutant (hereinafter referred to as "$HU^{171A}$ protein"), then the waterLOGSY experiment was repeated, and the binding effect of the drug and the mutated $HU^{171A}$ protein disappeared, proving that a key binding site of the two was the amino acid at the $71^{st}$ site in the HU protein. Specific experimental steps and experimental results are as follows:

Experimental Steps

An appropriate amount of Belinostat (MedChemExpress Company) was weighed and dissolved in DMSO-d6 (Solarbio Science & Technology Co., Ltd.) to obtain a stock solution of Belinostat with a concentration of 100 mM for use. 480 μl of solution containing 10 μM of HU protein was taken, 20 μL of $D_2O$ was added and mixed evenly, the obtained solution was transferred into a nuclear magnetic resonance tube, and an HSQC spectrogram of the HU protein was recorded on a Brooke 600 MHz nuclear magnetic resonance spectrometer (Avance III). 1 μL of Belinostat stock solution was taken, added into the foregoing nuclear magnetic resonance tube and mixed evenly, and then an HSQC spectrogram was recorded again.

1 μL of the foregoing Belinostat stock solution was taken, 479 μL of buffer solution (300 mM of NaCl and 50 mM of $K_2HPO_4$, with the pH of 6.5) and 20 μL of $D_2O$ were added and mixed evenly, and then the obtained solution was transferred to the nuclear magnetic resonance tube for use. In addition, two parts of 1 μL of the foregoing Belinostat stock solution were taken, an appropriate amount of HU protein and $HU^{171A}$ protein were added respectively, then an appropriate amount of buffer solution and 20 μL of $D_2O$ were added respectively, so that the total volume of the solution was 500 μL, and the final protein concentration was 10 μm. After uniform mixing, the obtained solutions were transferred to nuclear magnetic resonance tubes for use. The foregoing three samples were put into the Brooke 600 MHz nuclear magnetic resonance spectrometer (Avance III) for waterLOGSY 1D NMR detection.

Experimental Results

Figure 6:
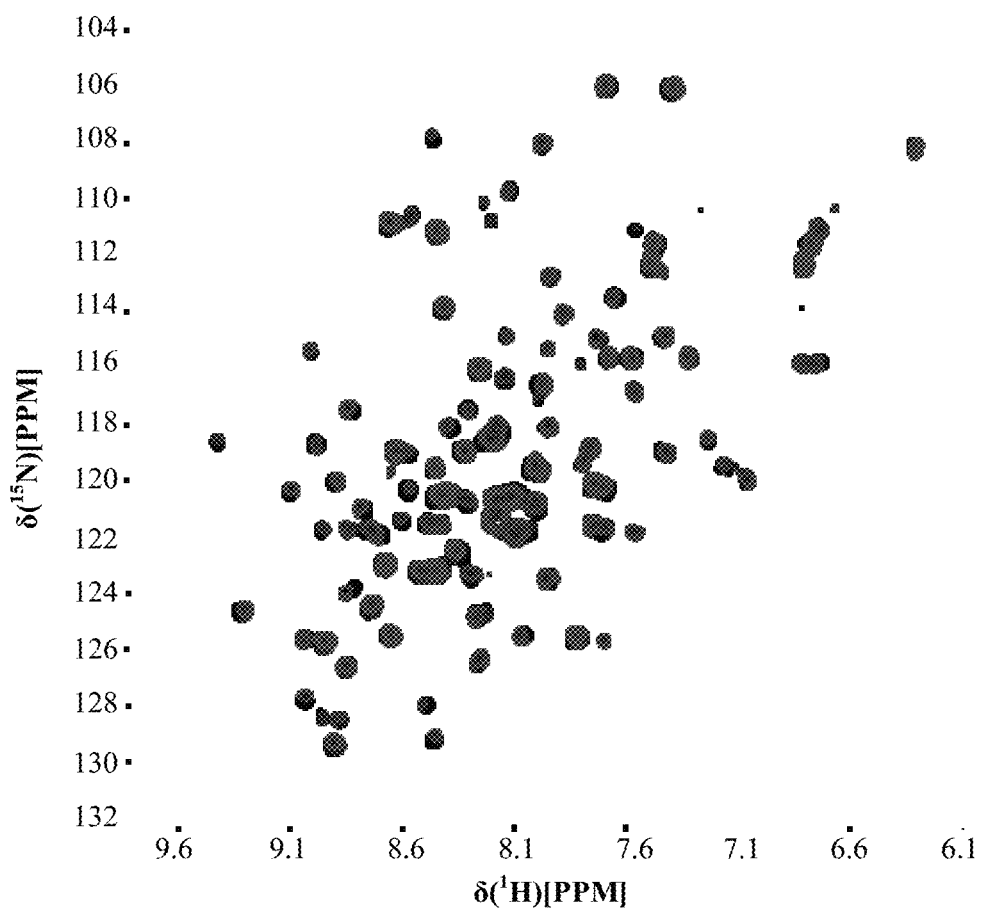
FIG. 6 illustrates that a nuclear magnetic Titration experiment proves that Belinostat can bind to a HU protein.
Figure 7:
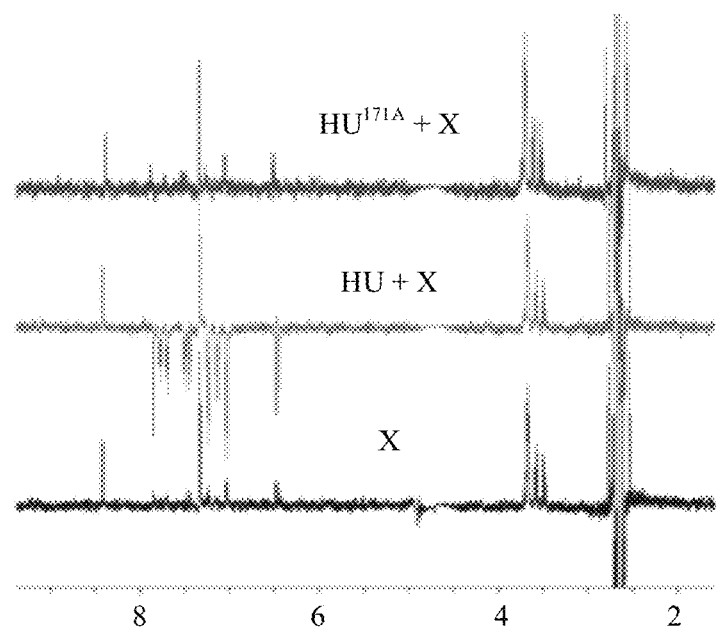
FIG. 7 illustrates that a waterLOGSY experiment proves that isoleucine at a 71st site of a HU protein is a key site for interaction between the protein and Belinostat (wherein "X" shown in the figure represents Belinostat)

Experimental Results are shown in FIG. 6 and FIG. 7. In FIG. 6, an original spectrum of the HU protein is gray, and a spectrum after adding of Belinostat is black. In FIG. 7, it may be learned that compared with the original spectrum, phenomena such as peak migration and peak intensity becoming stronger after adding of Belinostat appeared, indicating that Belinostat can bind to the HU protein.

According to the results shown in FIG. 7, it may be learned that: compared with the original waterLOGSY spectrogram of Belinostat, after the mixture of Belinostat with the HU protein, some peaks from Belinostat were reversed into negative peaks (positive peaks at 2.6 ppm, 3.7 ppm, and 8.5 ppm were from regions in which DMSO and Belinostat did not bind to the HU protein, respectively), indicating that Belinostat bound to the HU protein. After Belinostat was mixed with the foregoing mutated $HU^{171A}$ protein, the peak from Belinostat was still positive, and the spectrogram changed little, indicating that Belinostat could not react with the mutated HU protein, which proved that the isoleucine at the $71^{st}$ site in the HU protein was the key site for interaction with Belinostat.

Embodiment 3: A Cell-Level Experiment Proved an Inhibitory Effect of Belinostat on Bacteria Before the experiment, an appropriate amount of Belinostat was weighed and dissolved in DMSO to obtain a mother liquid with a concentration of 100 mM. The mother liquid was diluted with an LB medium for use. *Bacillus subtilis* used in this embodiment was ATCC 23857 strain, and *Staphylococcus aureus* was methicillin-resistant *Staphylococcus aureus* ATCC BAA-1761 strain.

3.1 Determining of a Growth Curve of *Bacillus subtilis*

Experimental Steps

The experiment was performed on a 96-well plate, four groups of drug treated groups and one blank control group (that is, the Control group) were set, and each group had three repeat wells. A bacterial solution of *Bacillus subtilis* (ATCC 23857 strain) cultured in an LB medium was diluted to 5×10$^5$ CFU/mL with an LB medium, 15 wells were selected in the middle of the 96-well plate, 100 μL of diluted bacterial solution was added to each well, and then 100 μL of Belinostat solution diluted with the LB medium was added, so that the final drug concentrations in the four drug treated groups were 100 μM, 200 μM, 400 μM, and 500 μM, respectively. DMSO and the LB medium were added to the blank control group, so that the final concentration of the DMSO was 0.5% and a volume of a reaction system was consistent with that of each drug treated group. Shaking culture was performed at 37° C. for 24 hours.

Absorbance at 600 nm was used as an index of a bacterial concentration in the culture solution for determining once every 3 hours. Finally, with $OD_{600}$ as a vertical coordinate and time as a horizontal coordinate, a bacterial growth curve was drawn.

Experimental Results

Figure 8:
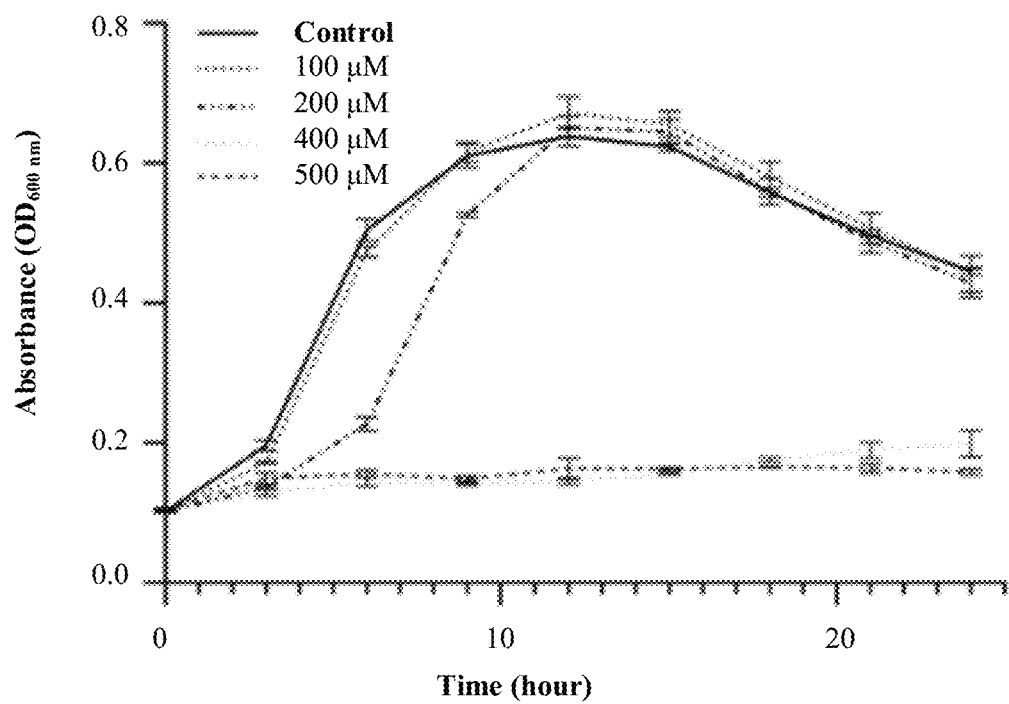
FIG. 8 illustrates growth curves of *Bacillus subtilis* in the presence of Belinostat at different concentrations.
Figure 9:
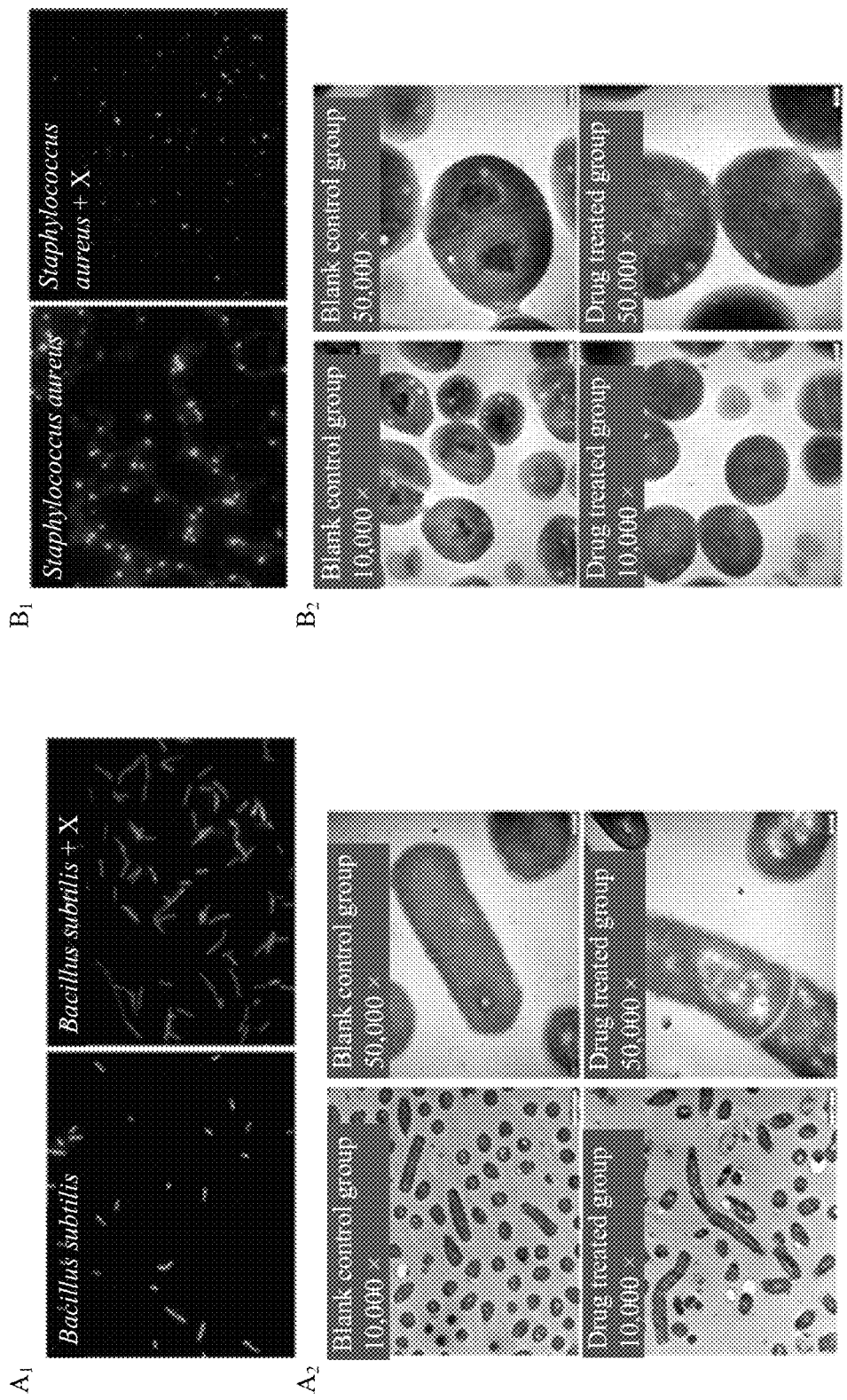
FIG. 9 illustrates an impact of Belinostat on morphologies of *Bacillus subtilis* and *Staphylococcus aureus*; FIG. $9A_1$ illustrates DAPI staining conditions of *Bacillus subtilis* (*B. subtilis*) before and after treatment with Belinostat (X); FIG. $9A_2$ illustrates transmission electron microscope images of *Bacillus subtilis* under different magnifications (specifically, 10,000 times and 50,000 times, respectively) before treatment with Belinostat (that is, a Control group) and after treatment with Belinostat (that is, a Treated group); FIG. $9B_1$ illustrates DAPI staining conditions of *Staphylococcus aureus* (*S. aureus*) before and after treatment with Belinostat (X); FIG. $9B_2$ illustrates transmission electron microscope images of *Staphylococcus aureus* under different magnifications (specifically, 10,000 times and 50,000 times, respectively) before treatment with Belinostat (that is, a Control group) and after treatment with Belinostat (that is, a Treated group)

As shown in FIG. 8, different concentrations of Belinostat have an inhibitory effect on growth of *Bacillus subtilis*. The absorbance of the bacterial solution treated with 200 μM Belinostat was lower than that of the blank control group for a long time, indicating that Belinostat had a relatively strong inhibitory effect on bacterial growth. After treatment with 400 μM and 500 μM Belinostat, bacteria growth was almost completely inhibited.

3.2 Bacterial DAPI Staining and Transmission Electron Microscope Observation

Experimental Steps

1) DAPI Staining

The experiments were performed in EP tubes, and one drug treated group and one blank control group were set. A bacterial solution of *Bacillus subtilis* cultured in an LB medium was diluted to 5×10$^5$ CFU/mL with the LB medium, 100 μL of diluted bacterial solution was taken and added to a 1.5 mL EP tube, and then 100 μL of Belinostat solution diluted with the LB medium was added, so that the final drug concentration was 500 μM. DMSO and the LB medium were added to the blank control group, so that the final concentration of the DMSO was 0.5% and a volume of a reaction system was consistent with that of the drug treated group. Three replicate tube were set in each group, and shaking culture was performed at 37° C. for 4 hours.

DAPI staining was performed on the *Bacillus subtilis* treated with Belinostat and the blank control group: (1) bacteria were collected by centrifugation, a supernatant was remove, the bacteria were resuspended in 1 mL of PBS, rinsed, and then centrifuged to collect the bacteria, and the supernatant was removed; (2) the bacteria were resuspended with 100 μL of 4% paraformaldehyde, and fixed at room temperature for 10 min; (3) the bacteria were collected by centrifugation, the supernatant was removed, the bacteria were resuspended with 1 mL of PBS, rinsed, and then centrifuged to collect the bacteria, and the supernatant was removed; (4) the bacteria were resuspended with 100 μL of 0.05% Triton X and then permeabilized at room temperature for 10 min; (5) the bacteria were collected by centrifugation, the supernatant was removed, the bacteria were resuspended in 1 mL of PBS, rinsed, and centrifuged to collect the bacteria, and the supernatant was removed; (6) the bacteria were resuspended with 10 μL of DAPI staining solution, and stained at room temperature for 10 min in the dark; and (7) the stained bacterial solution was applied to a glass slide, dried naturally in the dark, and observed and photographed under a fluorescence microscope.

Referring to the foregoing operation steps of DAPI staining for *Bacillus subtilis*, the *Bacillus subtilis* was replaced with *Staphylococcus aureus* (ATCC BAA-1761 strain), and the *Staphylococcus aureus* underwent DAPI staining.

2) Sample Preparation by Using a Transmission Electron Microscope

A bacterial solution of *Bacillus subtilis* cultured in an LB medium was diluted to $5 \times 10^5$ CFU/mL with the LB medium, 2.5 mL of diluted bacterial solution was taken and added to a 15 mL centrifuge tube, and then 2.5 mL of Belinostat solution diluted with the LB medium was added, so that the final drug concentration was 500 μM. 25 μL of DMSO and an appropriate amount of LB medium were added to the blank control group (the Control group) to ensure that a volume of a reaction system was consistent with that of the drug treated group (the Treated group). Three replicate tubes were set in each group. Shaking culture was performed at 37° C. for 4 hours, and bacteria were collected by centrifugation. After the supernatant was removed, the bacteria were fixed with 1 mL/dL glutaraldehyde at 4° C. for 1 hour, rinsed with PBS for 3 times (10 min each time), and fixed by osmic acid, underwent gradient dehydration with series-concentration acetone+ethanol (dehydration for 10 min for each concentration), embedding by an epoxy resin, ultra-thin sectioning, and lead-uranium electron staining, and then transmission electron microscopy observation was performed. The specific operation of the foregoing gradient dehydration with series-concentration acetone+ethanol (also referred to as a "gradient ethanol-acetone series dehydration method") was as follows: Dehydration was performed once with ethanol having concentrations of 30%, 50%, 70%, and 90% separately first, then dehydration was performed once with a 1:1 solution (100% anhydrous acetone:100% anhydrous ethanol), and finally dehydration was performed with 100% anhydrous acetone for 3 times. The treatment of *Staphylococcus aureus* was the same as above.

Experimental Results

DAPI staining results of *Bacillus subtilis* and *Staphylococcus aureus* are shown in FIG. $9A_1$ and FIG. $9 B_1$ respectively. It may be learned that a fluorescence region of *Bacillus subtilis* increased after treatment with Belinostat, indicating that a bacterial nucleus region became longer, and the cells became longer obviously. A fluorescence intensity of *Staphylococcus aureus* weakened after treatment with Belinostat, indicating that a bacterial nucleus region was dispersed.

Under a transmission electron microscope, it may also be clearly learned that compared with the control group, lengths of *Bacillus subtilis* treated with Belinostat were increased to different degrees, and nucleoid regions were scattered in many places in cytoplasm (FIG. $9A_2$). Nucleoid regions of *Staphylococcus aureus* treated with Belinostat became inconspicuous and showed a loose state (FIG. $9B_2$).

Experimental Results directly indicate that Belinostat can affect normal structures of nucleoid regions of two different bacteria, thereby inhibiting normal growth of bacteria, indicating that Belinostat has a broad-spectrum antibacterial ability.

Embodiment 4: An Animal Experiment Proved a Therapeutic Effect of Belinostat on a Bacterial Infection of Skin On the basis of the foregoing molecular experiments and cell experiments, inhibitory and therapeutic effects of Belinostat on a bacterial infection were further verified in an animal experiment.

(1) Experimental Materials

Medical tape; 3% chloral hydrate; normal saline; 0.1 μM Belinostat and 100 μM Belinostat (with solvents being 10% glycerin); a commercially available fusidic acid ointment (2% drug content); an LB plate; an independent air supply cage for mice; surgical scissors; tweezers; and a hair removal device.

20 female BALB/c mice aged 6-8 weeks were kept in the independent air supply cage.

Preparation of a bacterial solution: *Staphylococcus aureus* (ATCC BAA-1761 strain), preserved by the Laboratory Department of the First Affiliated Hospital of Xi'an Jiaotong University. Before the experiment, *Staphylococcus aureus* was inoculated in 5 mL of LB and placed in an incubator at 37° C. for shaking culture, and when the amount of bacteria was about $10^7$ CFU/mL, the bacteria were taken out for use.

(2) A TAP (Tape Stripping) Method was Used to Destroy a Skin Barrier of the Mice, and a model of superficial skin injury of the mice was established.

Back skin of 6-8 week-old female BALB/c mice was depilated with a depilatory paste before modeling, and an exposed skin region with a size of about 1 cm² was formed. On the day of modeling, the mice were anesthetized by intraperitoneal injection of 3% chloral hydrate at 10 mL/kg. A same operator pasted the medical adhesive tape to the depilated skin of the mice with basically a same strength, and then tore the medical adhesive tape off. The foregoing paste-tear operation was repeated many times to remove stratum corneum, and the adhesive tape needed to be replaced during each paste-tear process. When the skin of the mice became red and shiny, but there was no regular bleeding, the paste was stopped. The foregoing 10 μL of bacterial suspension was evenly applied to the damaged skin of the mice, and the infection lasted for 24 hours to establish the model of superficial skin injury of the mice.

(3) Verification of the Model by Using Local Therapeutic Drugs

The mice were randomly divided into four groups, which were a blank control (control) group, a low-concentration X group (low-concentration group, with a specific concentration of 0.1 μM), a high-concentration X group (high-concentration group, with a specific concentration of 100 μM), and a fusidic acid group (fusidic acid group, that is, a positive control group), with five mice in each group. All the mice of the blank control group were killed the day before the start of treatment to quantify an amount of bacterial inoculation. The three drug groups were administered twice a day (8:00 am. and 8:00 p.m. respectively) for three consecutive days after the infection. Dosages of the low-concentration X group and the high-concentration X group were 50 μL/time for each mouse, and a dosage of the fusidic acid group was 0.1 g/time for each mouse. Food intake, water consumption, and mental states of the mice were observed at least twice a day. After the experiment, the mice were killed.

(4) Examination of a Viable Bacterial Count on an Infected Wound

After the mice were killed, a wound of about 1 cm² was excised immediately, and put into a tissue homogenizing tube with 1 mL of normal saline and magnetic beads for tissue homogenization. 100 μL of tissue homogenate was diluted with normal saline for $10^1$, $10^2$, $10^3$, and $10^4$ times gradient, and then 100 μL of each diluted solution was evenly spread on an LB plate. After inverted overnight culture for 12-24 hours, colonies were counted and the count was converted into bacterial content (CFU/cm²) per square centimeter of tissue.

Figure 10:
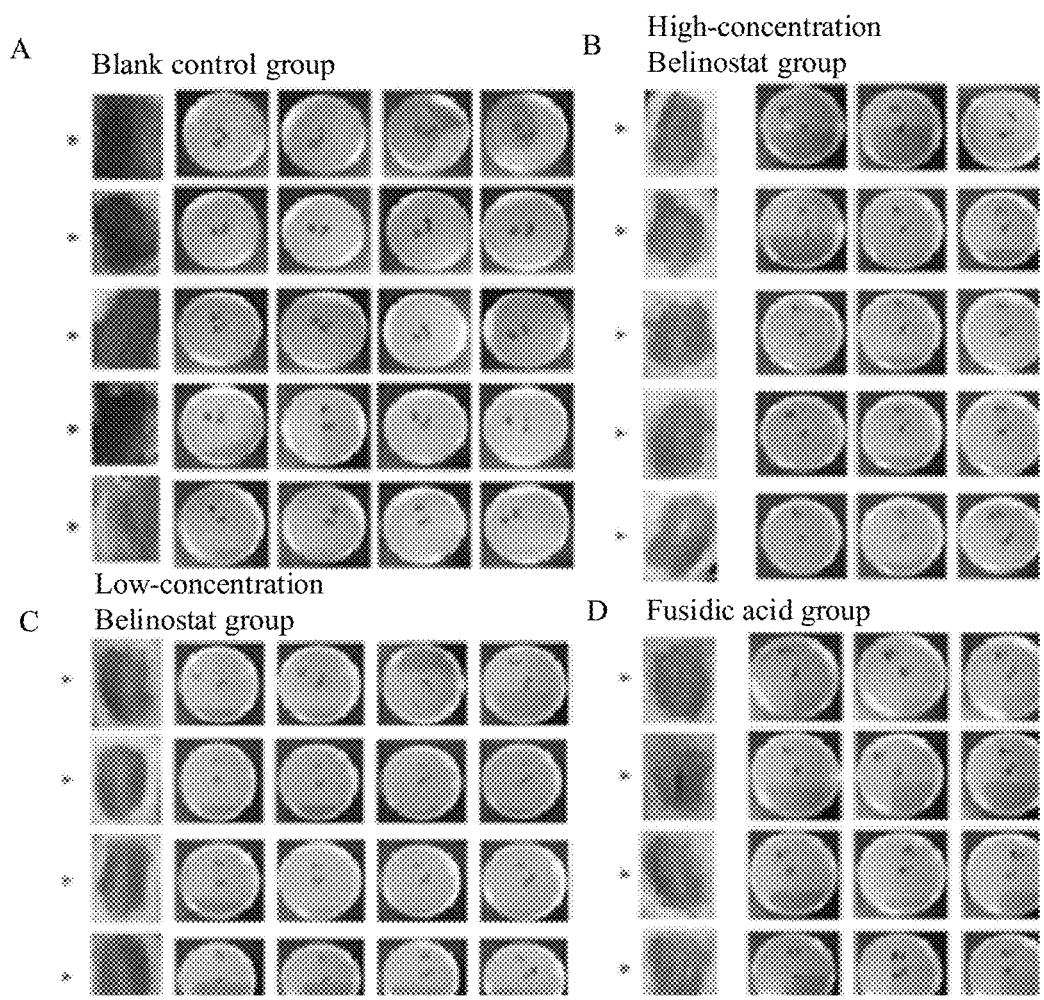
FIG. 10 illustrates bacterial infection conditions of skin of mice in each group.
Figure 11:
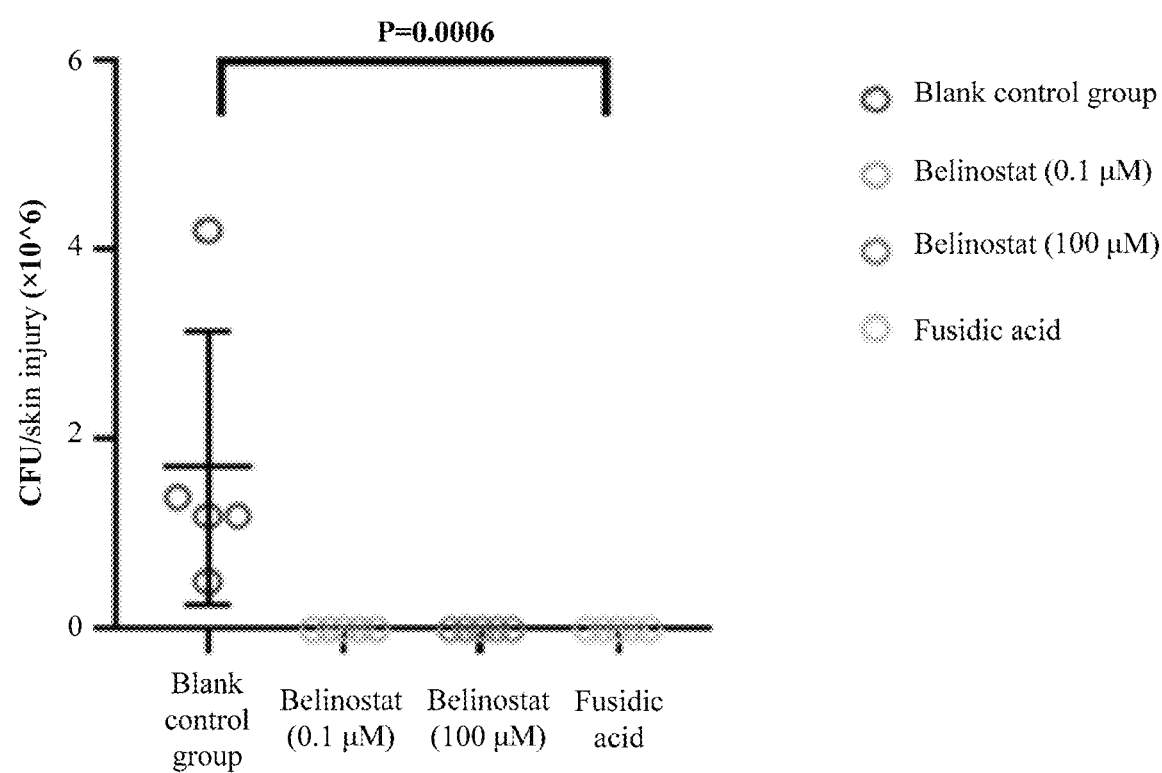
FIG. 11 illustrates statistical processing of a viable bacterial count on an infected wound.

Experimental Results (1) As shown in FIG. 10, after treatment with Belinostat and fusidic acid for 3 days, compared with those of the blank control group, a bacterial count in a skin lesion site of the mice was significantly reduced, and a quantity of colonies was statistically significant (as shown in FIG. 11, p.value=0.0006<0.01).

(2) In terms of a wound healing effect (as shown in FIG. 10), a wound healing speed of the low-concentration X group was significantly faster than that of the high-concentration X group and that of the fusidic acid group. This may be because Belinostat is an anticancer drug and has an ability to inhibit cell growth, so that a higher drug concentration indicates a slower wound healing speed. However, it may be learned from a bacterial load at the skin lesion site that the drugs at two concentrations have the same bactericidal effect, and can reduce the bacterial load of the wound.

In accordance with embodiments of the present application, Belinostat used in this experiment is of a non-ointment type, and a viscosity thereof is much lower than that of the positive control group (fusidic acid ointment), Belinostat had a good curative effect. According to test results, when the dosage of Belinostat was lower than that of the commercial fusidic acid, Belinostat showed an equivalent antibacterial ability, showing that Belinostat has strong prospects for development.

In view of the different dosage forms of Belinostat and the fusidic acid used in the experiment, the amounts of the drug substances were compared as parameters: $n_{Fusidic\ acid}=0.1\times0.02/516.345=3.87\times10^{-6}$ mol; $n_{Low\text{-}concentration\ Belinostat\ group}=0.1\times10^{-6}\times50\times10^{-6}=5\times10^{-12}$ mol; and $n_{High\text{-}concentration\ Belinostat\ group}=100\times10^{-6}\times50\times10^{-6}=5\times10^{-9}$ mol. It may be learned that the dosages of Belinostat in the high-concentration drug group and the low-concentration drug group were much lower than that of the fusidic acid, but the curative effect of Belinostat was better than that of the fusidic acid.

The specific embodiments enumerated in the present invention are only used as examples of the present invention, and the present invention is not limited to the specific embodiments described. For a person skilled in the art, any equivalent modification and replacement to the described embodiments also fall within the scope of the present invention. Therefore, equivalent changes and modifications made without departing from the spirit and scope of the present invention should fall within the scope of the present invention.

What is claimed is:

1. A preparation of a drug for treating an infection comprising Belinostat or a pharmaceutically acceptable salt thereof, wherein:
the drug is a tablet, a capsule, a granule, a syrup, a suspension, a solution, a dispersant, a sustained-release preparation for oral or non-oral administration, an intravenous preparation, a subcutaneous preparation, an inhalant, a transdermal preparation, or a rectal or vaginal suppository;
the infection is caused by one or more bacteria out of *Bacillus subtilis*, *Mycobacterium tuberculosis*, *Staphylococcus aureus*, or *Acinetobacter baumannii*; and
the infection is a skin infection, a gastrointestinal infection, a urinary tract infection, a genitourinary tract infection, a respiratory tract infection, a sinus infection, a middle ear infection, a systemic infection, a wound infection, a central nervous system infection, an intra-abdominal infection, pyelonephritis, pneumonia, bacterial vaginosis, streptococcal sore throat, chronic bacterial prostatitis, a gynecological and pelvic infection, a sexually transmitted bacterial disease, or eye and ear infections.

2. A method for treating an infection, the method comprising administering a composition comprising a therapeutically effective amount of Belinostat or a pharmaceutically acceptable salt thereof to a subject, wherein:
the composition is a tablet, a capsule, a granule, a syrup, a suspension, a solution, a dispersant, a sustained-release preparation for oral or non-oral administration, an intravenous preparation, a subcutaneous preparation, an inhalant, a transdermal preparation, or a rectal or vaginal suppository;
the infection is caused by one or more bacteria out of *Bacillus subtilis*, *Mycobacterium tuberculosis*, *Staphylococcus aureus*, or *Acinetobacter baumannii*; and
the infection is a skin infection, a gastrointestinal infection, a urinary tract infection, a genitourinary tract infection, a respiratory tract infection, a sinus infection, a middle ear infection, a systemic infection, a wound infection, a central nervous system infection, an intra-abdominal infection, pyelonephritis, pneumonia, bacterial vaginosis, streptococcal sore throat, chronic bacterial prostatitis, a gynecological and pelvic infection, a sexually transmitted bacterial disease, or eye and ear infections.

3. A pharmaceutical composition for treating an infection comprising Belinostat or a pharmaceutically acceptable salt thereof and a pharmaceutically acceptable carrier, wherein:
the composition is a tablet, a capsule, a granule, a syrup, a suspension, a solution, a dispersant, a sustained-release preparation for oral or non-oral administration, an intravenous preparation, a subcutaneous preparation, an inhalant, a transdermal preparation, or a rectal or vaginal suppository;
the infection is caused by one or more bacteria out of *Bacillus subtilis, Mycobacterium tuberculosis, Staphylococcus aureus,* or *Acinetobacter baumannii*; and
the infection is a skin infection, a gastrointestinal infection, a urinary tract infection, a genitourinary tract infection, a respiratory tract infection, a sinus infection, a middle ear infection, a systemic infection, a wound infection, a central nervous system infection, an intra-abdominal infection, pyelonephritis, pneumonia, bacterial vaginosis, streptococcal sore throat, chronic bacterial prostatitis, a gynecological and pelvic infection, a sexually transmitted bacterial disease, or eye and ear infections.

4. A preparation of an HU protein inhibitor for treating an infection, the preparation comprising Belinostat or a pharmaceutically acceptable salt thereof, wherein:
the preparation is a tablet, a capsule, a granule, a syrup, a suspension, a solution, a dispersant, a sustained-release preparation for oral or non-oral administration, an intravenous preparation, a subcutaneous preparation, an inhalant, a transdermal preparation, or a rectal or vaginal suppository;
the infection is caused by one or more bacteria out of *Bacillus subtilis, Mycobacterium tuberculosis, Staphylococcus aureus,* or *Acinetobacter baumannii*; and
the infection is a skin infection, a gastrointestinal infection, a urinary tract infection, a genitourinary tract infection, a respiratory tract infection, a sinus infection, a middle ear infection, a systemic infection, a wound infection, a central nervous system infection, an intra-abdominal infection, pyelonephritis, pneumonia, bacterial vaginosis, streptococcal sore throat, chronic bacterial prostatitis, a gynecological and pelvic infection, a sexually transmitted bacterial disease, or eye and ear infections.

5. A preparation of a drug for treating an infection comprising Belinostat or a pharmaceutically acceptable salt thereof, wherein:
the drug is a tablet, a capsule, a granule, a syrup, a suspension, a solution, a dispersant, a sustained-release preparation for oral or non-oral administration, an intravenous preparation, a subcutaneous preparation, an inhalant, a transdermal preparation, or a rectal or vaginal suppository;
the infection is caused by one or more bacteria out of *Staphylococcus aureus, Streptococcus pneumoniae, Streptococcus pyogenes, Streptococcus agalactiae, Enterococcus faecalis,* or *Enterococcus faecium;*
the infection is a skin infection, a gastrointestinal infection, a urinary tract infection, a genitourinary tract infection, a respiratory tract infection, a sinus infection, a middle ear infection, a systemic infection, a wound infection, a central nervous system infection, an intra-abdominal infection, pyelonephritis, pneumonia, bacterial vaginosis, streptococcal sore throat, chronic bacterial prostatitis, a gynecological and pelvic infection, a sexually transmitted bacterial disease, or eye and ear infections.

6. A preparation of a drug for treating an infection comprising Belinostat or a pharmaceutically acceptable salt thereof, wherein:
the drug is a tablet, a capsule, a granule, a syrup, a suspension, a solution, a dispersant, a sustained-release preparation for oral or non-oral administration, an intravenous preparation, a subcutaneous preparation, an inhalant, a transdermal preparation, or a rectal or vaginal suppository;
the infection is caused by bacteria resistant to one or more antibiotics;
the infection is a skin infection, a gastrointestinal infection, a urinary tract infection, a genitourinary tract infection, a respiratory tract infection, a sinus infection, a middle ear infection, a systemic infection, a wound infection, a central nervous system infection, an intra-abdominal infection, pyelonephritis, pneumonia, bacterial vaginosis, streptococcal sore throat, chronic bacterial prostatitis, a gynecological and pelvic infection, a sexually transmitted bacterial disease, or eye and ear infections.

7. The preparation according to claim 6, wherein the infection is caused by bacteria resistant to tetracycline or any member of first and second generation tetracycline antibiotics.

8. The preparation according to claim 6, wherein the infection is caused by bacteria resistant to methicillin.

9. The preparation according to claim 6, wherein the infection is caused by bacteria resistant to vancomycin.

10. The preparation according to claim 6, wherein the infection is caused by bacteria resistant to a quinolone or a fluoroquinolone.

11. The preparation according to claim 6, wherein the infection is caused by bacteria resistant to tigecycline or any other tetracycline derivative.

12. The preparation according to claim 6, wherein the infection is caused by bacteria resistant to beta-lactams or cephalosporins or bacteria resistant to penems or carbapenems.

13. The preparation according to claim 6, wherein the infection is caused by bacteria resistant to macrolide, lincosamides, streptogramins, oxazolidone, and pleuromutilin.

14. A method for treating an infection, the method comprising administering a composition comprising a therapeutically effective amount of Belinostat or a pharmaceutically acceptable salt thereof to a subject, wherein:
the composition is a tablet, a capsule, a granule, a syrup, a suspension, a solution, a dispersant, a sustained-release preparation for oral or non-oral administration, an intravenous preparation, a subcutaneous preparation, an inhalant, a transdermal preparation, or a rectal or vaginal suppository;
the infection is caused by one or more bacteria out of *Staphylococcus aureus, Streptococcus pneumoniae, Streptococcus pyogenes, Streptococcus agalactiae, Enterococcus faecalis,* or *Enterococcus faecium*; and
the infection is a skin infection, a gastrointestinal infection, a urinary tract infection, a genitourinary tract infection, a respiratory tract infection, a sinus infection, a middle ear infection, a systemic infection, a wound infection, a central nervous system infection, an intra-abdominal infection, pyelonephritis, pneumonia, bacterial vaginosis, streptococcal sore throat, chronic bacterial prostatitis, a gynecological and pelvic infection, a sexually transmitted bacterial disease, or eye and ear infections.

15. A pharmaceutical composition for treating an infection comprising Belinostat or a pharmaceutically acceptable salt thereof and a pharmaceutically acceptable carrier, wherein:
the composition is a tablet, a capsule, a granule, a syrup, a suspension, a solution, a dispersant, a sustained-release preparation for oral or non-oral administration, an intravenous preparation, a subcutaneous preparation, an inhalant, a transdermal preparation, or a rectal or vaginal suppository;
the infection is caused by one or more bacteria out of *Staphylococcus aureus, Streptococcus pneumoniae, Streptococcus pyogenes, Streptococcus agalactiae, Enterococcus faecalis,* or *Enterococcus faecium*; and
the infection is a skin infection, a gastrointestinal infection, a urinary tract infection, a genitourinary tract infection, a respiratory tract infection, a sinus infection, a middle ear infection, a systemic infection, a wound infection, a central nervous system infection, an intra-abdominal infection, pyelonephritis, pneumonia, bacterial vaginosis, streptococcal sore throat, chronic bacterial prostatitis, a gynecological and pelvic infection, a sexually transmitted bacterial disease, or eye and ear infections.

16. A preparation of an HU protein inhibitor for treating an infection, the preparation comprising Belinostat or a pharmaceutically acceptable salt thereof, wherein:
the preparation is a tablet, a capsule, a granule, a syrup, a suspension, a solution, a dispersant, a sustained-release preparation for oral or non-oral administration, an intravenous preparation, a subcutaneous preparation, an inhalant, a transdermal preparation, or a rectal or vaginal suppository;
the infection is caused by one or more bacteria out of *Staphylococcus aureus, Streptococcus pneumoniae, Streptococcus pyogenes, Streptococcus agalactiae, Enterococcus faecalis,* or *Enterococcus faecium*; and
the infection is a skin infection, a gastrointestinal infection, a urinary tract infection, a genitourinary tract infection, a respiratory tract infection, a sinus infection, a middle ear infection, a systemic infection, a wound infection, a central nervous system infection, an intra-abdominal infection, pyelonephritis, pneumonia, bacterial vaginosis, streptococcal sore throat, chronic bacterial prostatitis, a gynecological and pelvic infection, a sexually transmitted bacterial disease, or eye and ear infections.

17. A preparation of a drug for treating an infection comprising Belinostat or a pharmaceutically acceptable salt thereof, wherein:
the drug is a tablet, a capsule, a granule, a syrup, a suspension, a solution, a dispersant, a sustained-release preparation for oral or non-oral administration, an intravenous preparation, a subcutaneous preparation, an inhalant, a transdermal preparation, or a rectal or vaginal suppository;
the infection is caused by one or more bacteria out of *Haemophilus influenzae, Moraxella catarrhalis,* or *Legionella pneumophila*; and
the infection is a skin infection, a gastrointestinal infection, a urinary tract infection, a genitourinary tract infection, a respiratory tract infection, a sinus infection, a middle ear infection, a systemic infection, a wound infection, a central nervous system infection, an intra-abdominal infection, pyelonephritis, pneumonia, bacterial vaginosis, streptococcal sore throat, chronic bacterial prostatitis, a gynecological and pelvic infection, a sexually transmitted bacterial disease, or eye and ear infections.

18. A method for treating an infection, the method comprising administering a composition comprising a therapeutically effective amount of Belinostat or a pharmaceutically acceptable salt thereof to a subject, wherein:
the composition is a tablet, a capsule, a granule, a syrup, a suspension, a solution, a dispersant, a sustained-release preparation for oral or non-oral administration, an intravenous preparation, a subcutaneous preparation, an inhalant, a transdermal preparation, or a rectal or vaginal suppository;
the infection is caused by one or more bacteria out of *Haemophilus influenzae, Moraxella catarrhalis,* or *Legionella pneumophila*; and
the infection is a skin infection, a gastrointestinal infection, a urinary tract infection, a genitourinary tract infection, a respiratory tract infection, a sinus infection, a middle ear infection, a systemic infection, a wound infection, a central nervous system infection, an intra-abdominal infection, pyelonephritis, pneumonia, bacterial vaginosis, streptococcal sore throat, chronic bacterial prostatitis, a gynecological and pelvic infection, a sexually transmitted bacterial disease, or eye and ear infections.

19. A pharmaceutical composition for treating an infection comprising Belinostat or a pharmaceutically acceptable salt thereof and a pharmaceutically acceptable carrier, wherein:
the composition is a tablet, a capsule, a granule, a syrup, a suspension, a solution, a dispersant, a sustained-release preparation for oral or non-oral administration, an intravenous preparation, a subcutaneous preparation, an inhalant, a transdermal preparation, or a rectal or vaginal suppository;
the infection is caused by one or more bacteria out of *Haemophilus influenzae, Moraxella catarrhalis,* or *Legionella pneumophila*; and
the infection is a skin infection, a gastrointestinal infection, a urinary tract infection, a genitourinary tract infection, a respiratory tract infection, a sinus infection, a middle ear infection, a systemic infection, a wound infection, a central nervous system infection, an intra-abdominal infection, pyelonephritis, pneumonia, bacterial vaginosis, streptococcal sore throat, chronic bacterial prostatitis, a gynecological and pelvic infection, a sexually transmitted bacterial disease, or eye and ear infections.

20. A preparation of an HU protein inhibitor for treating an infection, the preparation comprising Belinostat or a pharmaceutically acceptable salt thereof, wherein:
the preparation is a tablet, a capsule, a granule, a syrup, a suspension, a solution, a dispersant, a sustained-release preparation for oral or non-oral administration, an intravenous preparation, a subcutaneous preparation, an inhalant, a transdermal preparation, or a rectal or vaginal suppository;
the infection is caused by one or more bacteria out of *Haemophilus influenzae, Moraxella catarrhalis,* or *Legionella pneumophila*; and
the infection is a skin infection, a gastrointestinal infection, a urinary tract infection, a genitourinary tract infection, a respiratory tract infection, a sinus infection, a middle ear infection, a systemic infection, a wound infection, a central nervous system infection, an intra-abdominal infection, pyelonephritis, pneumonia, bacterial vaginosis, streptococcal sore throat, chronic bacterial prostatitis, a gynecological and pelvic infection, a sexually transmitted bacterial disease, or eye and ear infections.

* * * * *

SEQUENCE LISTING

```
Sequence total quantity: 27
SEQ ID NO: 1            moltype = AA  length = 91
FEATURE                 Location/Qualifiers
source                  1..91
                        mol_type = protein
                        organism = Bacillus subtilis
SEQUENCE: 1
MNKTELINAV AESELSKKDA TKAVDSVFDT ILDALKNGDK IQLIGFGNFE VRERSARKGR    60
NPQTGEEIEI PASKVPAFKP GKALKDAVAG K                                   91

SEQ ID NO: 2            moltype = AA  length = 90
FEATURE                 Location/Qualifiers
source                  1..90
                        mol_type = protein
                        organism = Staphylococcus aureus
SEQUENCE: 2
MNKTDLINAV AEQADLTKKE AGSAVDAVFE SIQNSLAKGE KVQLIGFGNF EVRERAARKG    60
RNPQTGKEID IPASKVPAFK AGKALKDAVK                                     90

SEQ ID NO: 3            moltype = AA  length = 90
FEATURE                 Location/Qualifiers
source                  1..90
                        mol_type = protein
                        organism = Escherichia coli
SEQUENCE: 3
MNKSQLIDKI AAGADISKAA AGRALDAIIA SVTESLKEGD DVALVGFGTF AVKERAARTG    60
RNPQTGKEIT IAAAKVPSFR AGKALKDAVN                                     90
```

```
SEQ ID NO: 4                   moltype = AA   length = 90
FEATURE                        Location/Qualifiers
source                         1..90
                               mol_type = protein
                               organism = Klebsiella pneumoniae
SEQUENCE: 4
MNKSQLIDKI AAGADISKAA AGRALDALIA SVTESLQAGD DVALVGFGTF AVKERAARTG    60
RNPQTGKEIT IAAAKVPGFR AGKALKDAVN                                    90

SEQ ID NO: 5                   moltype = AA   length = 91
FEATURE                        Location/Qualifiers
source                         1..91
                               mol_type = protein
                               organism = Clostridium tetani
SEQUENCE: 5
MNKSELITSM AEKSKLTKKD AELVLKAFIE TVEETLETGE KVALVGFGTF ETRKRAARIG    60
RNPKTKEEIQ IPESTVPVFK PGKEFKERVN K                                  91

SEQ ID NO: 6                   moltype = AA   length = 92
FEATURE                        Location/Qualifiers
source                         1..92
                               mol_type = protein
                               organism = Clostridium botulinum
SEQUENCE: 6
MNKSELITSM AEKSKLTKKD AETALKAFIE SVEEALEGGE KVQLVGFGTF ETRERAERVG    60
RNPRTKEEIT IPASIAPVFK AGKELKEKVN KK                                 92

SEQ ID NO: 7                   moltype = AA   length = 90
FEATURE                        Location/Qualifiers
source                         1..90
                               mol_type = protein
                               organism = Bacillus cereus
SEQUENCE: 7
MNKTELTKVV AEKAELTQKD AAAATQAVLD TITTALASEE KVQILGFGTF EVRERSARTG    60
RNPQTGEEMQ IAASKVPAFK AGKELKDAVK                                    90

SEQ ID NO: 8                   moltype = AA   length = 90
FEATURE                        Location/Qualifiers
source                         1..90
                               mol_type = protein
                               organism = Bacillus anthracis
SEQUENCE: 8
MNKTELIKNV AQNAEISQKE ATVVVQTVVE SITNTLAAGE KVQLIGFGTF EVRERAARTG    60
RNPQTGEEMQ IAASKVPAFK AGKELKEAVK                                    90

SEQ ID NO: 9                   moltype = AA   length = 90
FEATURE                        Location/Qualifiers
source                         1..90
                               mol_type = protein
                               organism = Acinetobacter baumannii
SEQUENCE: 9
MNKSELIDAI AEKGGVSKTD AGKALDATIA SITEALKKGD TVTLVGFGTF SVKERAARTG    60
RNPKTGEELQ IKATKVPSFK AGKGLKDSVA                                    90

SEQ ID NO: 10                  moltype = AA   length = 10
FEATURE                        Location/Qualifiers
source                         1..10
                               mol_type = protein
                               organism = Bacillus subtilis
SEQUENCE: 10
EIPASKVPAF                                                          10

SEQ ID NO: 11                  moltype = AA   length = 10
FEATURE                        Location/Qualifiers
source                         1..10
                               mol_type = protein
                               organism = Staphylococcus aureus
SEQUENCE: 11
DIPASKVPAF                                                          10

SEQ ID NO: 12                  moltype = AA   length = 10
FEATURE                        Location/Qualifiers
source                         1..10
                               mol_type = protein
                               organism = Escherichia coli
SEQUENCE: 12
TIAAAKVPSF                                                          10
```

```
SEQ ID NO: 13              moltype = AA   length = 10
FEATURE                    Location/Qualifiers
source                     1..10
                           mol_type = protein
                           organism = Klebsiella pneumoniae
SEQUENCE: 13
TIAAAKVPGF                                                                10

SEQ ID NO: 14              moltype = AA   length = 10
FEATURE                    Location/Qualifiers
source                     1..10
                           mol_type = protein
                           organism = Clostridium tetani
SEQUENCE: 14
QIPESTVPVF                                                                10

SEQ ID NO: 15              moltype = AA   length = 10
FEATURE                    Location/Qualifiers
source                     1..10
                           mol_type = protein
                           organism = Clostridium botulinum
SEQUENCE: 15
TIPASIAPVF                                                                10

SEQ ID NO: 16              moltype = AA   length = 10
FEATURE                    Location/Qualifiers
source                     1..10
                           mol_type = protein
                           organism = Bacillus cereus
SEQUENCE: 16
QIAASKVPAF                                                                10

SEQ ID NO: 17              moltype = AA   length = 10
FEATURE                    Location/Qualifiers
source                     1..10
                           mol_type = protein
                           organism = Bacillus anthracis
SEQUENCE: 17
QIAASKVPAF                                                                10

SEQ ID NO: 18              moltype = AA   length = 10
FEATURE                    Location/Qualifiers
source                     1..10
                           mol_type = protein
                           organism = Acinetobacter baumannii
SEQUENCE: 18
QIKATKVPSF                                                                10

SEQ ID NO: 19              moltype = AA   length = 92
FEATURE                    Location/Qualifiers
source                     1..92
                           mol_type = protein
                           organism = Bacillus subtilis
SEQUENCE: 19
MNKSELIKQV AIQSELTKPQ ASLAVDAVLE SIQHALQNGE HVQLLGFGTF EVRERAAREG         60
RNPHTGEALR IPAGKTPAFK AGKALKEAVK AK                                       92

SEQ ID NO: 20              moltype = AA   length = 90
FEATURE                    Location/Qualifiers
source                     1..90
                           mol_type = protein
                           organism = Staphylococcus aureus
SEQUENCE: 20
MNKTDLINAV AEQADLTKKE AGSAVDAVFE SIQNSLAKGE KVQLIGFGNF EVRERAARKG         60
RNPQTGKEID IPASKVPAFK AGKALKDAVK                                          90

SEQ ID NO: 21              moltype = AA   length = 90
FEATURE                    Location/Qualifiers
source                     1..90
                           mol_type = protein
                           organism = Escherichia coli
SEQUENCE: 21
MNKSQLIDKI AAGADISKAA AGRALDAIIA SVTESLKEGD DVALVGFGTF AVKERAARTG         60
RNPQTGKEIT IAAAKVPSFR AGKALKDAVN                                          90

SEQ ID NO: 22              moltype = AA   length = 90
FEATURE                    Location/Qualifiers
source                     1..90
```

```
                                mol_type = protein
                                organism = Klebsiella pneumoniae
SEQUENCE: 22
MNKSQLIDKI AAGADISKAA AGRALDALIA SVTESLQAGD DVALVGFGTF AVKERAARTG    60
RNPQTGKEIT IAAAKVPGFR AGKALKDAVN                                    90

SEQ ID NO: 23                   moltype = AA  length = 91
FEATURE                         Location/Qualifiers
source                          1..91
                                mol_type = protein
                                organism = Clostridium tetani
SEQUENCE: 23
MNKSELITSM AEKSKLTKKD AELVLKAFIE TVEETLETGE KVQLVGFGTF ETRKRAARIG    60
RNPKTKEEIQ IPESTVPVFK PGKEFKERVN K                                  91

SEQ ID NO: 24                   moltype = AA  length = 92
FEATURE                         Location/Qualifiers
source                          1..92
                                mol_type = protein
                                organism = Clostridium botulinum
SEQUENCE: 24
MNKSELITSM AEKSKLTKKD AETALKAFIE SVEEALEGGE KVQLVGFGTF ETRERAERVG    60
RNPRTKEEIT IPASIAPVFK AGKELKEKVN KK                                 92

SEQ ID NO: 25                   moltype = AA  length = 90
FEATURE                         Location/Qualifiers
source                          1..90
                                mol_type = protein
                                organism = Bacillus cereus
SEQUENCE: 25
MNKTELTKVV AEKAELTQKD AAAATQAVLD TITTALASEE KVQILGFGTF EVRERSARTG    60
RNPQTGEEMQ IAASKVPAFK AGKELKDAVK                                    90

SEQ ID NO: 26                   moltype = AA  length = 90
FEATURE                         Location/Qualifiers
source                          1..90
                                mol_type = protein
                                organism = Bacillus anthracis
SEQUENCE: 26
MNKTELIKNV AQNAEISQKE ATVVVQTVVE SITNTLAAGE KVQLIGFGTF EVRERAARTG    60
RNPQTGEEMQ IAASKVPAFK AGKELKEAVK                                    90

SEQ ID NO: 27                   moltype = AA  length = 90
FEATURE                         Location/Qualifiers
source                          1..90
                                mol_type = protein
                                organism = Acinetobacter baumannii
SEQUENCE: 27
MNKSELIDAI AEKGGVSKTD AGKALDATIA SITEALKKGD TVTLVGFGTF SVKERAARTG    60
RNPKTGEELQ IKATKVPSFK AGKGLKDSVA                                    90
```